(12) United States Patent
Yoon (10) Patent No.: US 11,925,542 B1
(45) Date of Patent: Mar. 12, 2024

(54) MESH ASSEMBLY FOR COSMETIC SURGERY

(71) Applicant: Sangjoon Yoon, Gwangju-si (KR)

(72) Inventor: Sangjoon Yoon, Gwangju-si (KR)

( * ) Notice: Subject to any disclaimer, the term of this patent is extended or adjusted under 35 U.S.C. 154(b) by 0 days.

(21) Appl. No.: 18/449,250

(22) Filed: Aug. 14, 2023

(51) Int. Cl.
*A61F 2/00* (2006.01)

(52) U.S. Cl.
CPC .......... *A61F 2/0059* (2013.01); *A61F 2/0077* (2013.01); *A61F 2002/0072* (2013.01); *A61F 2210/0004* (2013.01); *A61F 2220/0008* (2013.01); *A61F 2220/0025* (2013.01); *A61F 2230/0091* (2013.01)

(58) Field of Classification Search
CPC .................. A61F 2/0059; A61F 2/0077; A61F 2002/0072; A61F 2210/0004; A61F 2220/0008; A61F 2220/0025; A61F 2230/0091
See application file for complete search history.

(56) References Cited

U.S. PATENT DOCUMENTS

| | | | |
|---|---|---|---|
| 2006/0205995 A1* | 9/2006 | Browning | A61F 2/0063 600/29 |
| 2008/0161837 A1* | 7/2008 | Toso | A61F 2/0045 606/151 |
| 2010/0256442 A1* | 10/2010 | Ogdahl | A61F 2/0045 600/30 |
| 2013/0018395 A1* | 1/2013 | Friedlander | A61F 2/0063 606/151 |
| 2017/0360543 A1* | 12/2017 | Rosenblatt | A61B 17/06166 |

* cited by examiner

*Primary Examiner* — Thaddeus B Cox
*Assistant Examiner* — Joshua Daryl D Lannu
(74) *Attorney, Agent, or Firm* — Bridgeway IP Law Group, PLLC; Jihun Kim (57) ABSTRACT

A mesh assembly for cosmetic surgery that can be used for tissue lifting is proposed. The mesh assembly includes: a mesh sleeve that includes a multiple number of helical string members, which are entwined in intersecting directions to form a passage having a particular diameter within the mesh sleeve; a core that extends along a first direction and is positioned within the passage; and a protrusion that protrudes from the outer perimeter of the core in a direction inclined towards one side and extends through a gap between the string members to the outside of the mesh sleeve. The mesh assembly can have a drastically greater strength compared to a regular surgical thread and can also be joined to the surgical site with high strength, thus providing greater utility in procedures such as tissue lifting.

5 Claims, 9 Drawing Sheets

MESH ASSEMBLY FOR COSMETIC SURGERY

CROSS-REFERENCE TO RELATED APPLICATIONS

This application claims the benefit of Korean Patent Application No. 10-2023-0059541, filed with the Korean Intellectual Property Office on May 9, 2023, the disclosure of which is incorporated herein by reference in its entirety.

BACKGROUND

1. Technical Field

The present invention relates to a surgical tool, more particularly to a mesh assembly for cosmetic surgery that can be used for tissue lifting.

2. Description of the Related Art

With advances in surgical technology as well as an overall increase in the standard of living, there is a growing interest in cosmetic surgery. A typical example of cosmetic surgery is the facelift (rhytidectomy), which may involve tightening saggy skin or removing wrinkles.

Various techniques and tools have been developed for surgical procedures such as the facelift. One method frequently used in the past includes incising and removing skin tissue from the patient, pulling on the skin, and then suturing the incised area. A more current method uses a thread, where a thread inserted under the skin can be used to pull the tissue and thereby remove sagging and wrinkles. However, the thread may be ineffective in pulling the skin tissue, since the thread cannot be firmly attached to the tissue, and such a thread is also liable to break or become untied.

SUMMARY OF THE INVENTION

An aspect of the present invention, which was conceived to resolve the problem described above, is to provide a mesh assembly for cosmetic surgery that has a high strength and can be firmly attached to the surgical site for use in various types of cosmetic surgery.

Other objectives of the present invention will be more clearly understood from the embodiments set forth below.

A mesh assembly for cosmetic surgery according to an aspect of the invention can include: a mesh sleeve that includes a multiple number of helical string members, which are entwined in intersecting directions to form a passage having a particular diameter within the mesh sleeve; a core that extends along a first direction and is positioned within the passage; and a protrusion that protrudes from the outer perimeter of the core in a direction inclined towards one side and extends through a gap between the string members to the outside of the mesh sleeve.

A mesh assembly for cosmetic surgery according to an embodiment of the present invention can include one or more of the following features. For example, the mesh sleeve can be made from a hydrolysable material. The mesh sleeve can be made from a material containing one or more polymer selected from a group consisting of polydioxanone (PDO), polylactic acid (PLA), poly-L-lactide (PLLA), poly-caprolactone (PCL), polyhydroxyalkanoate (PHA), polyhydroxybutyrate (PHB), poly-D-lactide, and poly-DL-lactide (PDLLA).

The mesh assembly for cosmetic surgery can further include a cover film, which may be positioned between the mesh sleeve and the core, and which may surround the protrusion to restrain the protrusion such that the protrusion lies within the passage. When the cover film is removed after the mesh sleeve is inserted into a surgical site, the protrusion can protrude out of the mesh sleeve.

In certain embodiments, the cover film can be wound around the core in a helical form. In certain embodiments, the cover film can surround the core in a tube-like form.

An indentation can be formed in the core, and an end portion of the protrusion can have a curved portion formed in a curved shape on its outer side and has a hook portion formed in a pointy shape on its inner side. While the protrusion is restrained by the cover film, the hook portion of the protrusion can be inserted in the indentation and the curved portion can face the cover film.

The mesh assembly can further include a needle, which may extend along the first direction, and in which a channel space may be formed, where the needle can be configured to hold the mesh sleeve and the core within the channel space.

The needle can include a compressed portion, which may be compressed along a second direction that is orthogonal to the first direction, and a cross section of the channel space at the compressed portion can have a decreased width along the second direction and an increased width along a third direction that is orthogonal to both the first direction and the second direction.

The needle can include a rounded front end, and an opening communicating with the channel space can be formed in a side surface of the front end. Alternatively, the needle can include a front end having a cutaway portion along an acutely intersecting plane, and an opening communicating with the channel space can be formed in the cutaway portion.

The mesh assembly can further include a needle, to an end portion of which at least one of the mesh sleeve and the core may be coupled. For example, the mesh assembly can include two needles, the mesh sleeve and the core can extend to the same length, and the two needles can be coupled respectively to both ends of the mesh sleeve and the core. The needle can be a suture needle having a curved shape.

An embodiment of the present invention having the features above can provide various advantageous effects including the following. However, an embodiment of the present invention may not necessarily exhibit all of the effects below.

A mesh assembly according to an embodiment of the invention can have a drastically greater strength compared to a regular surgical thread and can also be joined to the surgical site with high strength, thus providing greater utility in procedures such as tissue lifting.

A mesh assembly according to an embodiment of the invention makes it possible to more precisely adjust the positions where the protrusions extending out of the mesh sleeve join the surrounding tissue at the surgical site and thus can significantly increase the success rate of the procedure.

DETAILED DESCRIPTION OF THE INVENTION

As the invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed by the present invention. In the description of the present invention, certain detailed explanations of the related art are omitted if it is deemed that they may unnecessarily obscure the essence of the invention.

The terms used in the present specification are merely used to describe particular embodiments and are not intended to limit the present invention. An expression used in the singular encompasses the expression of the plural, unless it has a clearly different meaning in the context. In the present specification, it is to be understood that terms such as "including" or "having," etc., are intended to indicate the existence of the features, numbers, steps, actions, components, parts, or combinations thereof disclosed in the specification and are not intended to preclude the possibility that one or more other features, numbers, steps, actions, components, parts, or combinations thereof may exist or may be added.

While such terms as "first" and "second," etc., can be used to describe various components, such components are not to be limited by the above terms. The above terms are used only to distinguish one component from another.

Certain embodiments of the present invention will be described below in more detail with reference to the accompanying drawings. Those components that are the same or are in correspondence are rendered the same reference numeral, and redundant descriptions are omitted.

Figure 1:
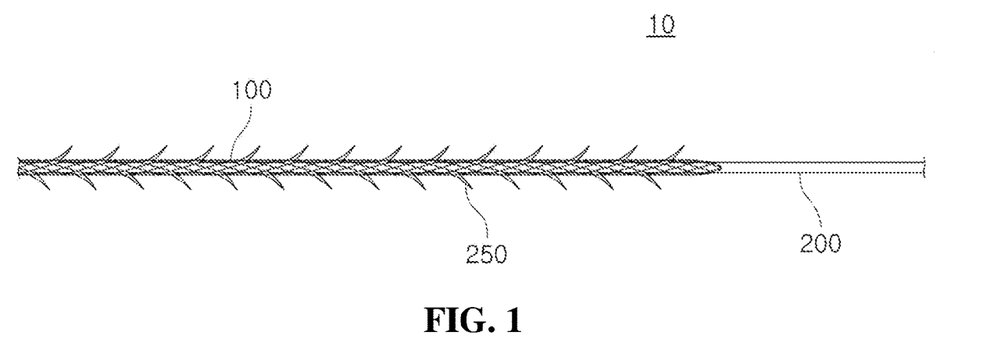
FIG. 1 is a side view illustrating a mesh assembly for cosmetic surgery according to a first disclosed embodiment of the invention.
Figure 2:
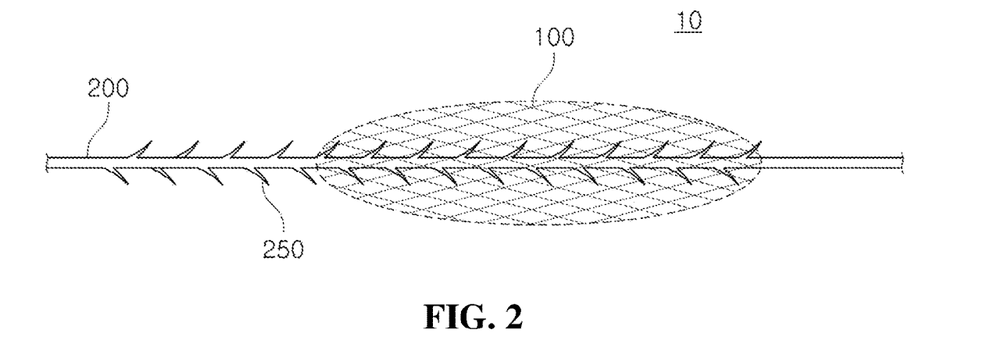
FIG. 2 is a side view illustrating the mesh assembly for cosmetic surgery shown in FIG. 1 with the mesh sleeve in an expanded form.
Figure 3A:
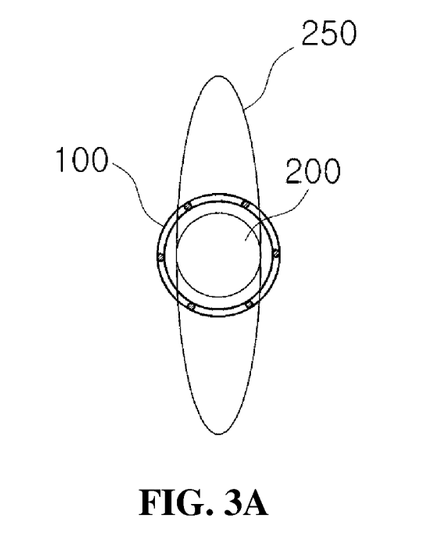
FIG. 3A is a rear cross-sectional view of the mesh assembly for cosmetic surgery shown in FIG. 1.
Figure 3B:
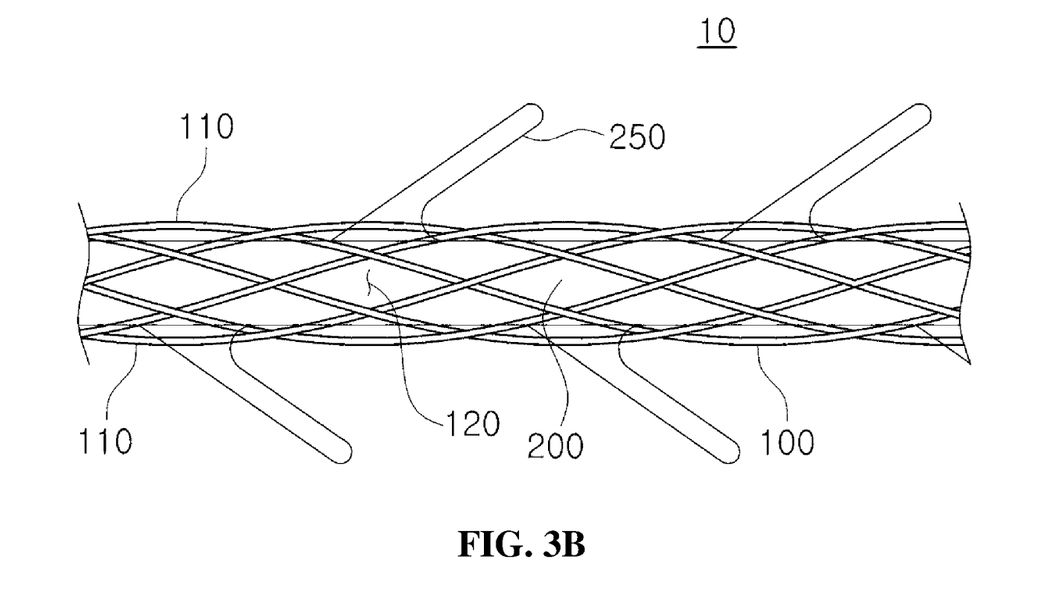
FIG. 3B is a magnified side view of the mesh assembly for cosmetic surgery shown in FIG. 1.

FIG. 1 and FIG. 2 are side views illustrating a mesh assembly 10 for cosmetic surgery according to a first disclosed embodiment of the invention, while FIG. 3A and FIG. 3B illustrate a portion of the mesh assembly 10 for cosmetic surgery according to the first disclosed embodiment.

Referring to FIGS. 1, 2, 3A, and 3B, a mesh assembly 10 for cosmetic surgery according to the first disclosed embodiment of the invention can mainly include a mesh sleeve 100, a core 200, and protrusions 250. A needle such as a cannula, suture needle, etc., can be provided on the front end of the mesh assembly 10 for cosmetic surgery, where either one or both of the mesh sleeve 100 and core 200 can be coupled to the needle.

The mesh sleeve 100 can include a multiple number of helical string members 110, which can be intertwined in intersecting directions to form a 3-dimensional shape. Of course, depending on the diameter required for the mesh sleeve 100, there can be additional string members included, other than the string members 110 that extend along helical paths. The mesh sleeve 100 can basically form a passage of a particular diameter on the inside and can thus form a shape similar to a cylinder. The mesh sleeve 100 can have an outer diameter of 1.8 mm to 4.5 mm, for example, but the invention is not limited by the diameter of the mesh sleeve 100.

The mesh sleeve 100 can be made from different materials depending on its usage, and in an embodiment of the invention, the mesh sleeve 100 can be made from a hydrolysable material. For example, the mesh sleeve 100 can be made from a material containing polydioxanone (PDO). Polydioxanone is a biocompatible polymer that can be degraded by hydrolysis, where most of its end products may be excreted in urine. Polydioxanone is typically degraded and eliminated within six months and is known not to incur foreign body reaction. Similarly, the mesh sleeve 100 can be made from a material containing one or more polymers of polylactic acid (PLA), poly-L-lactide (PLLA), polycaprolactone (PCL), polyhydroxyalkanoate (PHA), polyhydroxybutyrate (PHB), poly-D-lactide, and poly-DL-lactide (PDLLA).

The core 200 can extend in one direction, and at least a portion of the core 200 can be positioned within the mesh sleeve 100, i.e., in the passage of the mesh sleeve 100. The core 200 can be formed with a diameter smaller than the diameter of the passage of the mesh sleeve 100. The core 200 can have an outer diameter of 0.4 mm to 2.0 mm, for example, but the invention is not limited by the diameter of the core 200. Although FIG. 3A depicts the cross section of the core 200 as having a generally circular shape, the core 200 can be implemented with a flatter shape in certain embodiments. Of course, the invention is not limited by the cross section of the core 200, either.

The protrusions 250 can be configured such that each protrusion 250 protrudes from the outer perimeter of the core 200 in a direction inclined towards one side. In a preferred embodiment of the invention, the protrusions 250 can be formed in lengths that allow the end of each protrusion to extend to the outside of the mesh sleeve 100. That is, the protrusions 250 can pass through the spaces 120 formed in-between the string members 110 forming the mesh sleeve 100 such that the ends of the protrusions 250 are positioned outside the mesh sleeve 100.

Referring to FIGS. 3A and 3B, in a mesh assembly 10 according to an embodiment of the invention, the protrusions 250 can be formed on an upper portion and a lower portion of the core 200. That is, the protrusions 250 can protrude from the core 200 in just two directions. This makes it possible to place the core 200, on which the protrusions 250 are formed, in a flat orientation. Thus, the mesh assembly 10 can be applied so as not to protrude too much towards the front while inserted to the subcutaneous tissue of the patient, unless expanded intentionally.

Due to the composition of the protrusions 250 being inclined towards one side, it becomes difficult to move the mesh assembly 10 in said one side compared to the opposite side. That is, when the mesh assembly 10 is moved towards the one side, the ends of the protrusions 250 may be caught on the surrounding tissue such that movement is hindered, but when the mesh assembly 10 is moved towards the other side, the ends of the protrusions 250 may not be caught on the surrounding tissue, and movement may not be hindered. In consideration of this, the needle for the mesh assembly 10 can be coupled on the side that is in the opposite direction of the inclined direction of the protrusions 250.

In cases where a mesh assembly 10 according to an embodiment of the invention is used for suturing or tissue lifting, the protrusions 250 protruding out of the mesh sleeve 100 can be used to secure the mesh assembly 10 at a needed position. The protrusions 250 may serve to securely join the mesh assembly 10 to the tissue of the surgical site such that the mesh assembly 10 cannot not become detached. Thus, when the surgeon applies a force on the mesh assembly 10, the mesh assembly 10 may effectively pull the surrounding tissue.

Since the mesh sleeve 100 is formed from a multiple number of intertwined string members 110, the mesh sleeve 100 is able to resist a far greater tensile strength compared to a regular thread. Also, since the mesh sleeve 100 consists of string members 110 forming a 3-dimensional shape with large areas of space 120 left in-between the string members 110, the regenerating tissue at the surgical site can grow to the inside of the mesh sleeve 100, so that the mesh sleeve 100 can become integrated with the surgical site. In cases where the mesh sleeve 100 is made from a hydrolysable material, the mesh sleeve 100 can be degraded and removed from the body, and in cases where the mesh sleeve 100 is not made from a hydrolysable material, the mesh sleeve 100 can remain within the body as an implant.

As illustrated in FIG. 2, a mesh sleeve 100 according to an embodiment of the invention can be used in an expanded form. Since the mesh sleeve 100 is composed of intertwined string members 110, it is possible to expand the middle portion of the mesh sleeve 100 by pressing it from both the one side and the other side. This can be achieved, for example, by having the other side of the mesh sleeve 100 be caught on one of the protrusions 250 and then pressing the one side of the mesh sleeve 100. The expanded form of the mesh sleeve 100 can serve as an implant at the corresponding site. In certain embodiments, a functional agent such as a filler, etc., can be inserted inside the mesh sleeve 100.

Figure 4:
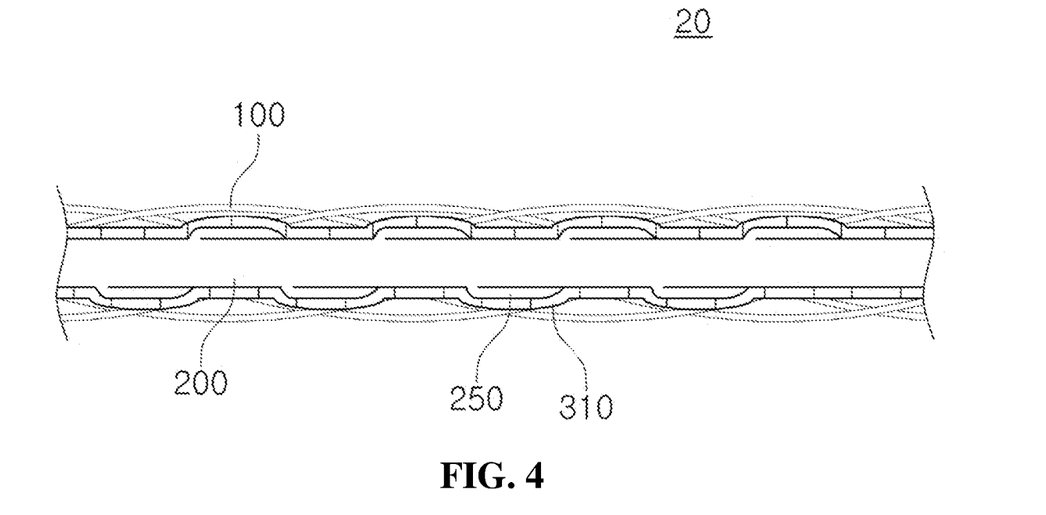
FIG. 4 is a cross-sectional view of a mesh assembly for cosmetic surgery according to a second disclosed embodiment of the invention.

FIG. 4 is a cross-sectional view of a mesh assembly 20 for cosmetic surgery according to a second disclosed embodiment of the invention. A mesh assembly 20 for cosmetic surgery based on the second disclosed embodiment of the invention has many features in common with the mesh assembly 10 for cosmetic surgery based on the first disclosed embodiment of the invention described above, and the descriptions that follow will focus mainly on the differences of the mesh assembly 20 based on the second disclosed embodiment. Features described for the first disclosed embodiment can be applied to the second disclosed embodiment, and likewise, features described for the second disclosed embodiment can be applied to the first disclosed embodiment. Certain reference numerals used in describing the second disclosed embodiment are intended to refer to components that correspond to the components having the same reference numerals in the first disclosed embodiment.

Referring to FIG. 4, a mesh assembly 20 for cosmetic surgery according to the second disclosed embodiment of the invention can mainly include a mesh sleeve 100, a core 200, protrusions 250, and a cover film 310. As the mesh sleeve 100, core 200, and protrusions 250 may be substantially the same as those described for the first disclosed embodiment, redundant descriptions will be omitted here.

The cover film 310 may correspond to a member that is placed between the mesh sleeve 100 and the core 200 to restrain the protrusions 250. The cover film 310 can surround the protrusions 250 such that the protrusions 250 cannot protrude out of the mesh sleeve 100 and such that the protrusions 250 remain positioned within the passage of the mesh sleeve 100. In the example illustrated in FIG. 4, the cover film 310 is implemented in a form that is wound around the core 200, and the cover film 310 restrains the protrusions 250 such that the protrusions 250 contact the core 200.

As described above in relation to the first disclosed embodiment, the protrusions 250 of the mesh assembly 10 can protrude out of the mesh sleeve 100 and can be inclined towards one side, so as to be caught on the surrounding tissue and be firmly joined. The protrusions 250 can also be used to secure the end of the mesh sleeve 100 on the other side when an expanding of the mesh sleeve 100 is required. Since the protrusions 250 formed on the core 200 are inclined towards one side, the protrusions 250 may not hinder the movement of the mesh assembly 10 towards the other side but may hinder movement towards the one side. As such, caution may be needed when arranging the mesh assembly 10 at the needed site, because if the mesh assembly 10 is moved beyond the needed position towards the other side, it may be difficult to adjust the position by moving the mesh assembly 10 back in the direction of the one side.

A mesh assembly 20 for cosmetic surgery according to the second disclosed embodiment of the invention can further include a cover film 310, which can prevent the protrusions 250 from hindering the movement of the mesh assembly 20. A surgeon using the mesh assembly 20 can insert the mesh assembly 20 into the surgical site with the cover film 310 arranged over the protrusions 250 between the mesh sleeve 100 and the core 200 and can remove the cover film 310 when the mesh sleeve 100 and the core 200 have been placed at the required position.

Since the cover film 310 is wound in a helical form, the surgeon can separate the cover film 310 by holding the end of the cover film 310 and rotating the cover film 310 around the core 200. As the cover film 310 is removed, the protrusions 250 can protrude out of the mesh sleeve 100 to be caught on the tissue surrounding the mesh assembly 20 and thus provide a high-strength joint.

Figure 5:
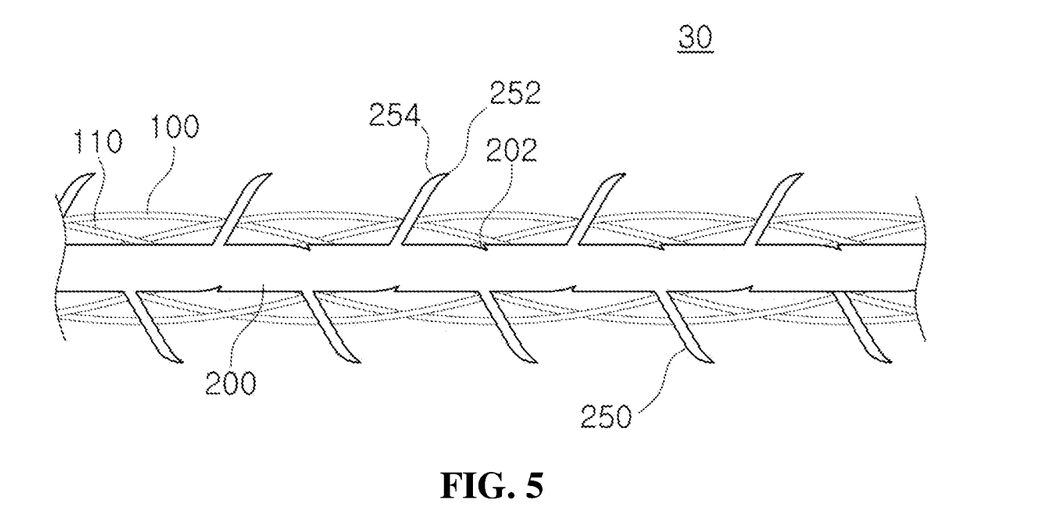
FIG. 5 is a cross-sectional view of a mesh assembly for cosmetic surgery according to a third disclosed embodiment of the invention.
Figure 6:
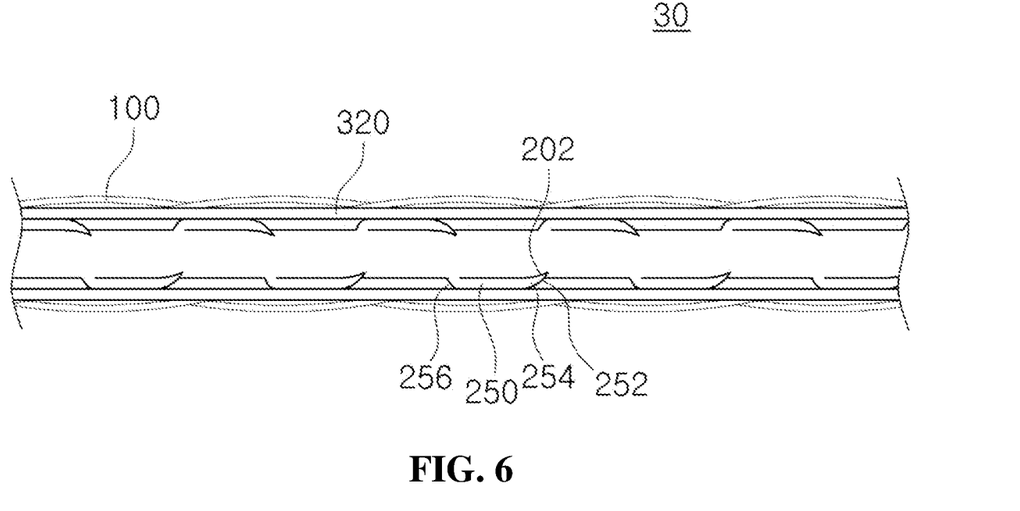
FIG. 6 is a cross-sectional view of a mesh assembly for cosmetic surgery according to a third disclosed embodiment of the invention.

FIG. 5 and FIG. 6 are cross-sectional views of a mesh assembly 30 for cosmetic surgery according to a third disclosed embodiment of the invention. A mesh assembly 30 for cosmetic surgery based on the third disclosed embodiment of the invention has many features in common with the mesh assemblies 10, 20 for cosmetic surgery based on the first and second disclosed embodiments of the invention described above, and the descriptions that follow will focus mainly on the differences of the mesh assembly 30 based on the third disclosed embodiment. Features described for the first and second disclosed embodiments can be applied to the third disclosed embodiment, and likewise, features described for the third disclosed embodiment can be applied to any of the first and second disclosed embodiments. Certain reference numerals used in describing the third disclosed embodiment are intended to refer to components that correspond to the components having the same reference numerals in the first and/or second disclosed embodiment.

Referring to FIG. 5 and FIG. 6, a mesh assembly 30 for cosmetic surgery according to the third disclosed embodiment of the invention can mainly include a mesh sleeve 100, a core 200, protrusions 250, and a cover film 320. As the mesh sleeve 100 may be substantially the same as the one described for the first disclosed embodiment, redundant descriptions will be omitted here.

In a mesh assembly 30 according to the third disclosed embodiment, the cover film 320 can have a tube-like form for surrounding the core 200, as in the illustration of FIG. 6. As the protrusions 250 and the core 200 are positioned within a cover film 320 having a designated width, the protrusions 250 may be pressed against the core 200, so as not to protrude out of the mesh sleeve 100 and not hinder the movement of the mesh assembly 30. A surgeon using the mesh assembly 20 can insert the mesh assembly 30 into the surgical site with the cover film 320 arranged over the protrusions 250 between the mesh sleeve 100 and the core 200 and can remove the cover film 320 when the mesh sleeve 100 and the core 200 have been placed at the required position.

Since the cover film 320 surrounds the core 200 and the protrusions 250 in a tube-like form, the surgeon can peel off the cover film 320 from the core 200 by holding the end of the cover film 320 and pulling the cover film 320 off. As the cover film 320 is removed, the protrusions 250 can protrude out of the mesh sleeve 100 to be caught on the tissue surrounding the mesh assembly 20 and thus provide a high-strength joint.

As illustrated in FIG. 5, a mesh assembly 30 according to the third disclosed embodiment of the invention can have the protrusions 250 formed such that the end portion of each protrusion 250 has a hook portion 252 formed on the inner side and a curved portion 254 formed on the outer side. The hook portion 252 can form a pointy edge in the form of a point or a line, while the curved portion 254 can form a gentle curve. Also, while the protrusions 250 are pressed against the core 200, the connecting portion 256 between the protrusion 250 and the core 200 can also form a gentle curve.

Indentations 202 can be formed in the core 200. The indentations 202 can be formed in a concave shape in positions separated by lengths corresponding to the protruding lengths of the protrusions 250 from the connecting portions 256 of the protrusions 250 and can be configured such that, when the protrusions 250 are pressed against the core 200, the hook portions 252 on the front ends of the protrusions 250 are inserted in the indentations 202.

Referring to FIG. 6, while the cover film 320 is surrounding the core 200 and protrusions 250 in a tube-like form, the hook portions 252 of the protrusions 250 can be inserted in the indentations 202 formed in the core 200, and only the curved portions 254 on the outer sides of the protrusions 250 can face the outer side. Thus, the connecting portions 256 and curved portions 254 of the protrusions 250 may face the outer side and contact the cover film 320, and the hook portions 252 of the protrusions 250 may not contact the cover film 320, so that when the surgeon pulls the cover film 320, the cover film 320 can move easily without any latching.

When the cover film 320 is pulled and removed from around the protrusions 250, the protrusions 250 can spread outward, to extend out of the mesh sleeve 100 as illustrated in FIG. 5 and be strongly joined to the tissue surrounding the mesh assembly 30. In order that the protrusions 250 may protrude outward more easily, the pitch of the helical string members 110 forming the mesh sleeve 100 can be proportional to the intervals of the protrusions 250.

In certain embodiments, the cover film 320 can also be made from a hydrolysable material or soluble material, in which case the protrusions 250 can be made to protrude outward after the mesh assembly 30 has been inserted when the cover film 320 is degraded by hydrolysis or dissolved at the surgical site.

Figure 7:
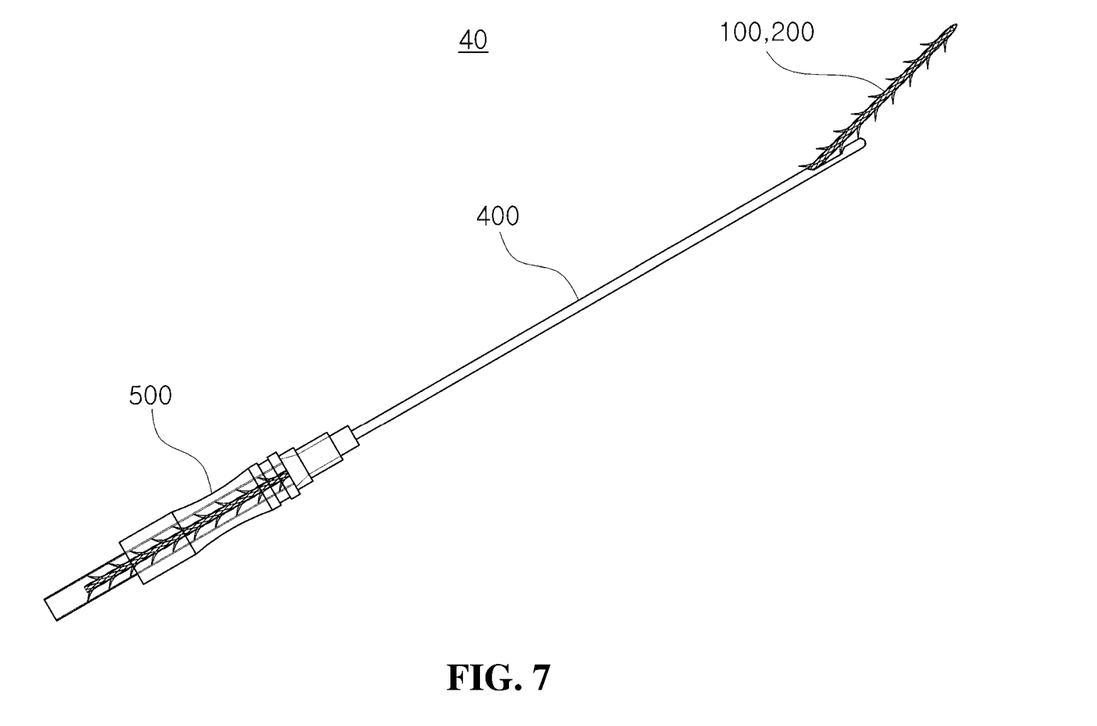
FIG. 7 is a side view of a mesh assembly for cosmetic surgery according to a fourth disclosed embodiment of the invention.

FIG. 7 is a side view of a mesh assembly 40 for cosmetic surgery according to a fourth disclosed embodiment of the invention. Referring to FIG. 7, a mesh assembly 40 for cosmetic surgery according to the fourth disclosed embodiment of the invention can include a needle 400 in addition to one of the mesh assemblies 10, 20, 30 for cosmetic surgery based on the first to third disclosed embodiments described above. That is, the mesh assembly 40 can include a mesh sleeve 100, a core 200, a cover film 310, 320, and a needle 400.

Regarding the direction in which the core 200 extends as a first direction, the needle 400 can extend along the first direction and can have a channel space 420 formed on the inside. In the present specification, the term "needle 400" is not limited to a hypodermic needle but rather encompasses any type of tool that has a channel space 420 on the inside, including cannulas, suture needles, catheters, etc.

The channel space 420 can continue from an opening 430 located at the rear end of the needle 400 to an opening 440 located at the front end of the needle 400. As illustrated in FIG. 7, the mesh sleeve 100, core 200, and cover film 310, 320 can be inserted in the channel space 420 of the needle 400. The mesh sleeve 100, core 200, and cover film 310, 320 can enter the opening 430 on the rear end side of the channel space 420 and can be inserted up to or beyond the opening 440 on the front end side. A connector 500 can further be provided on the rear end side of the needle 400 for convenience.

Figure 8:
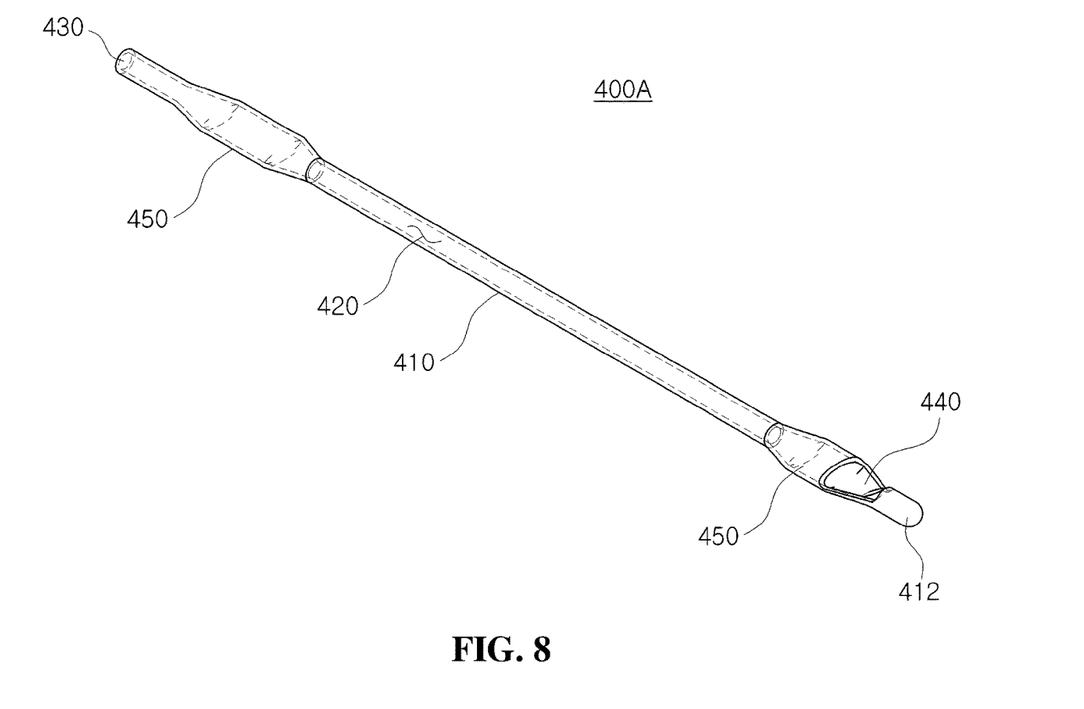
FIG. 8 is a perspective view of a needle for a mesh assembly for cosmetic surgery according to an embodiment of the invention.
Figure 9:
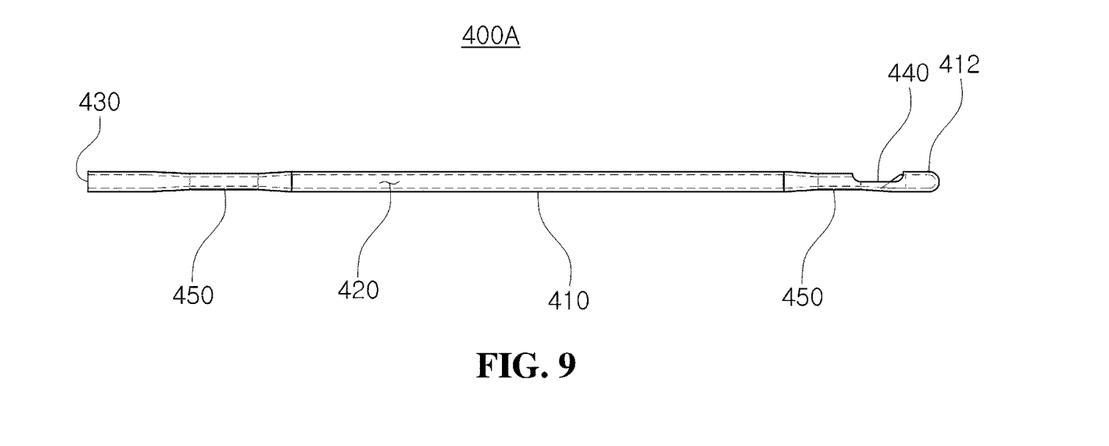
FIG. 9 is a side view of the needle shown in FIG. 8.

FIG. 8 and FIG. 9 illustrate a needle 400A that can be applied to a mesh assembly 40 for cosmetic surgery according to an embodiment of the invention. According to an embodiment of the invention, the needle 400A can include compressed portions 450. Here, the term "compressed portion 450" is used to convey the shape of the needle 400A and does not require that the body 410 of the needle 400A be actually compressed.

In the present specification, the direction in which the needle 400 extends is referred to as the first direction, a direction orthogonal to the first direction is referred to as a second direction, and a direction orthogonal to both the first direction and the second direction is referred to as a third direction. At a compressed portion 450, the body 410 of the needle 400 can be compressed along the second direction, so that the cross section of the body 410 may have a decreased width along the second direction and conversely an increased width along the third direction.

Since a mesh assembly 40 according to an embodiment of the invention is formed with protrusions 250 protruding from the core 200, the cross section of the core 200 including the protrusions 250 may have a width along one particular (e.g., the third direction) greater than a width along another direction (e.g., the second direction). If the needle 400 were to maintain a circular cross section for the channel space 420 and accommodate the mesh sleeve 100 and core 200 inside with an increased inner diameter, the overall diameter of the needle 400 can become excessively large, which would lead to the forming of larger holes in the surgical site of the patient and hence to a greater possibility of leaving a scar.

If the needle 400 is formed with compressed portions 450 as in an embodiment of the invention, the cross section of the channel space 420 may have a decreased width along the second direction and an increased width along the third direction, making it more suitable to accommodate the core 200 having a smaller width along the second direction and a greater width along the third direction. In an embodiment of the invention, it would be possible to form a compressed portion 450 by actually compressing a portion of a needle having a basic form such as an 18-gauge needle, for example.

In the example shown in FIG. 8 and FIG. 9, a multiple number of compressed portions 450 are formed on the needle 400. Of course, the locations and number of compressed portions 450 can be modified as needed. The front end 412 of the needle 400A may be rounded so as to include only a smooth curved surface without sharp edges. The front opening 440 of the channel space 420 can be formed on the side surface of the front end 412.

Figure 10:
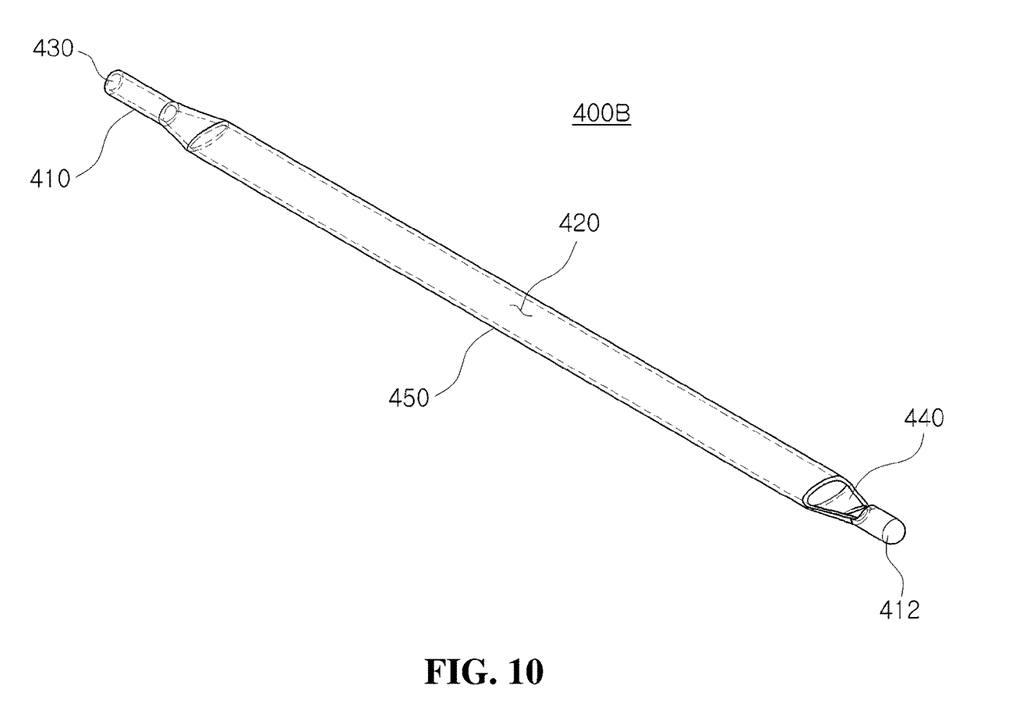
FIG. 10 is a perspective view of a needle for a mesh assembly for cosmetic surgery according to an embodiment of the invention.
Figure 11:
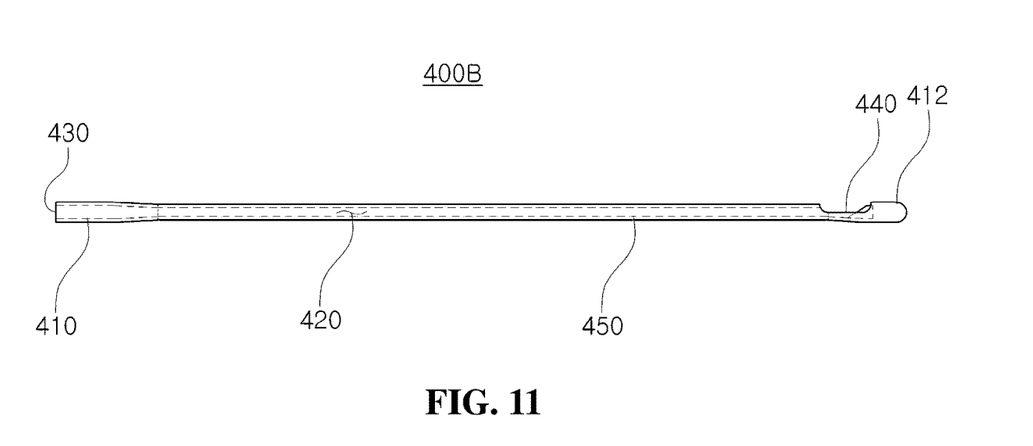
FIG. 11 is a side view of the needle shown in FIG. 10.

FIG. 10 and FIG. 11 illustrate another needle 400B that can be applied to a mesh assembly 40 for cosmetic surgery according to an embodiment of the invention. In the needle 400B illustrated in FIG. 10 and FIG. 11, the compressed portion 450 is formed over most of the body 410 of the needle, with the compressed portion 450 extending up to the front opening 440. In the needle 400B illustrated in FIG. 10 and FIG. 11, the rear end of the body 410 of the needle 400 maintains an uncompressed state, but in certain embodiments, the compressed portion 450 can be formed over the entire body 410 of needle 400, including the rear end portion.

Figure 12:
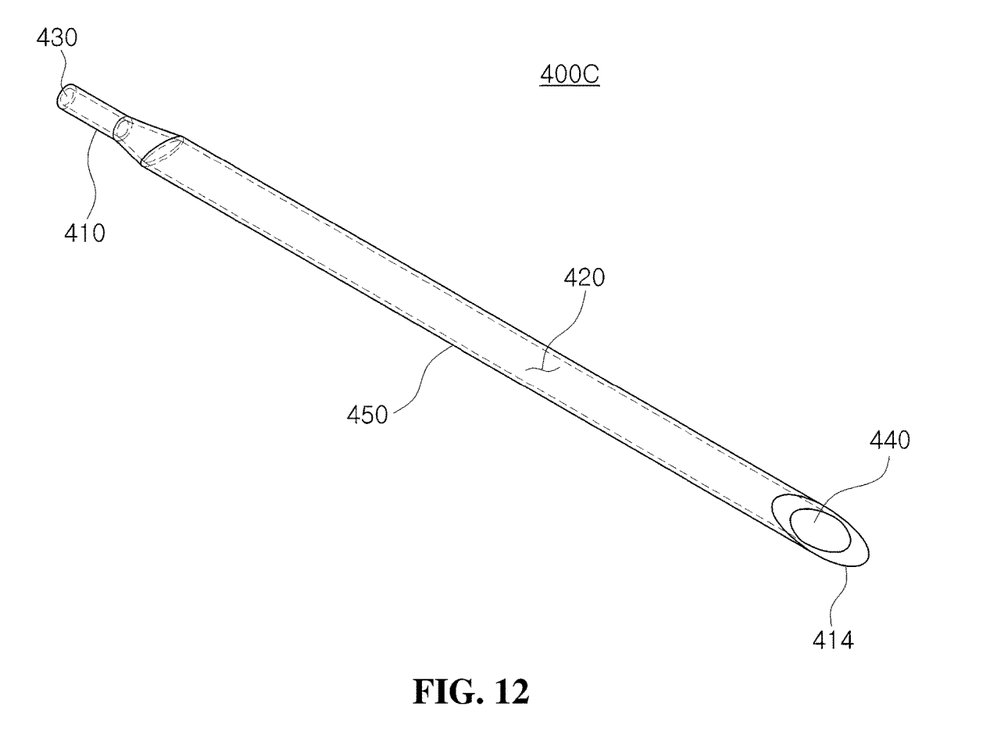
FIG. 12 is a perspective view of a needle for a mesh assembly for cosmetic surgery according to an embodiment of the invention.
Figure 13:
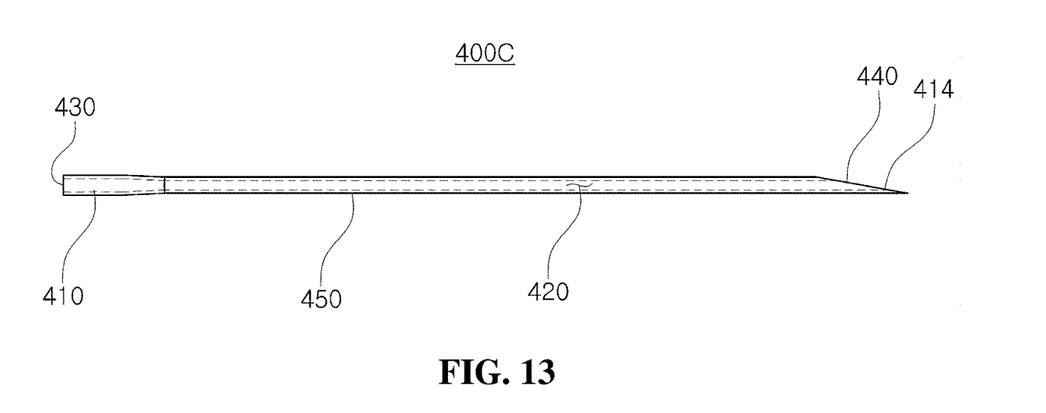
FIG. 13 is a side view of the needle shown in FIG. 12.

FIG. 12 and FIG. 13 illustrate another needle 400C that can be applied to a mesh assembly 40 for cosmetic surgery according to an embodiment of the invention. In the needle 400C illustrated in FIG. 12 and FIG. 13, the front end 414 of the needle 400 is formed with a cutaway portion along an acutely intersecting plane, and the front opening 440 of the channel space 420 is formed in the cutaway portion of the front end 414. This structure allows the compressed portion 450 to continue up to the front end 414.

Figure 14:
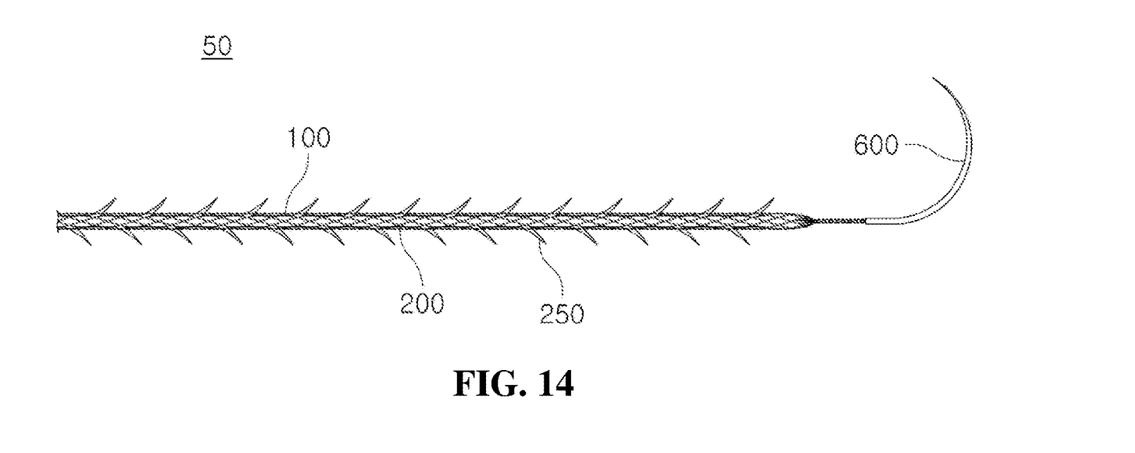
FIG. 14 is a side view of a mesh assembly for cosmetic surgery according to a fifth disclosed embodiment of the invention.
Figure 15:
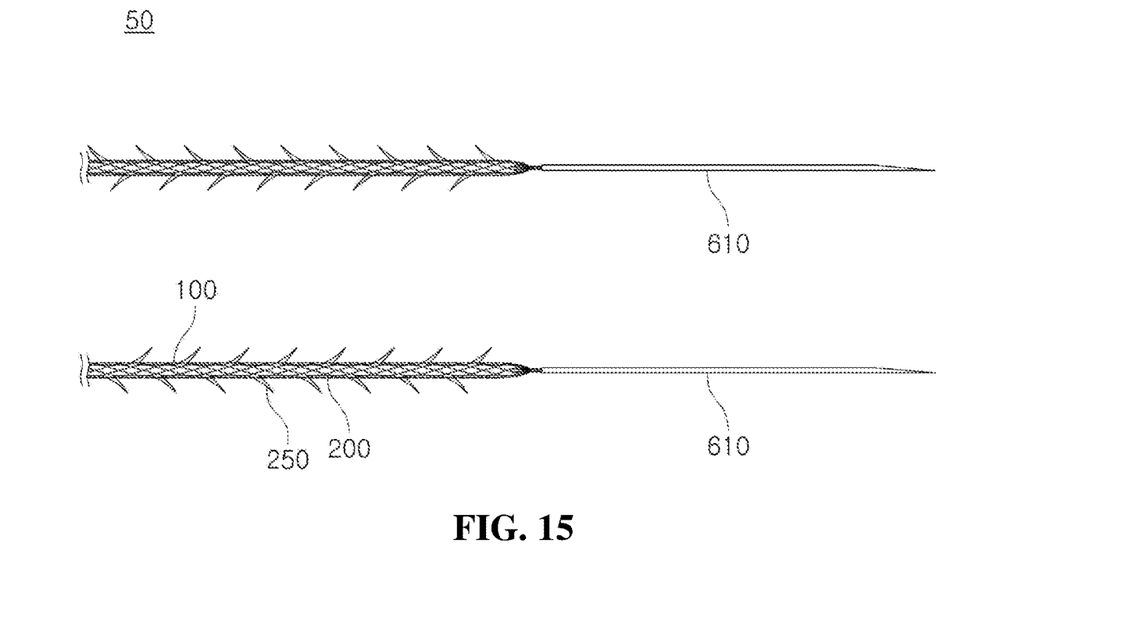
FIG. 15 is a side view of a mesh assembly for cosmetic surgery according to a fifth disclosed embodiment of the invention.

FIG. 14 and FIG. 15 are side views of a mesh assembly 50 for cosmetic surgery according to a fifth disclosed embodiment of the invention. Referring to FIG. 14 and FIG. 15, a mesh assembly 50 for cosmetic surgery according to the fifth disclosed embodiment of the invention can include at least one needle 600, 610 in addition to one of the mesh assemblies 10, 20, 30 for cosmetic surgery based on the first to third disclosed embodiments described above. That is, the mesh assembly 50 can include a mesh sleeve 100, a core 200, a cover film 310, 320, and a needle 600, 610.

At least one of the mesh sleeve 100 and the core 200 can be coupled to an end portion of the needle 600. That is, while the front ends of both the mesh sleeve 100 and the core 200 can be coupled to the rear end of the needle 600, it is also possible to have just the mesh sleeve 100 or just the core 200 coupled to the needle 600. The needle 600, 610 can have any of a variety of shapes as necessary. For example, the needle 600 in FIG. 14 has a curved shape in the manner of a suture needle, whereas the needle 610 in FIG. 15 has a linear shape in the manner of a basic needle. The needle 610 in FIG. 15 can have a length of about 100 mm to 400 mm.

As illustrated in FIG. 15, a mesh assembly 50 for cosmetic surgery according to the fifth disclosed embodiment of the invention can have needles 600, 610 coupled to both ends of the mesh sleeve 100 and core 200. For example, the mesh sleeve 100 and the core 200 can extend to the same length, and the needles 600, 610 can be coupled to both ends of the mesh sleeve 100 and the core 200.

Figure 16:
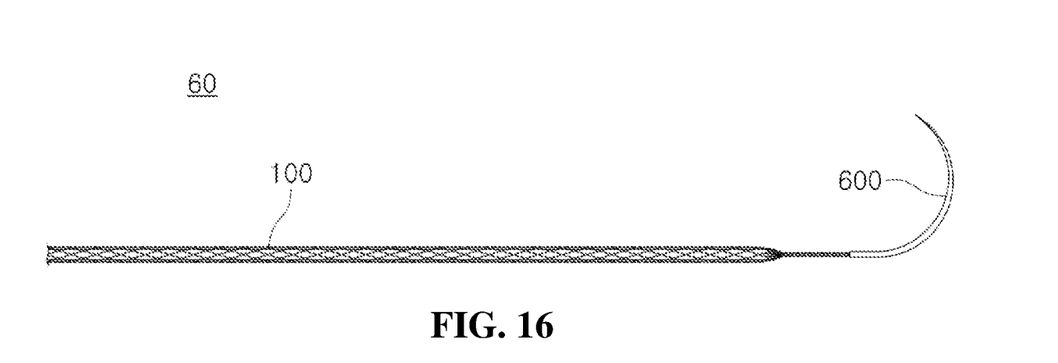
FIG. 16 is a side view of a mesh assembly for cosmetic surgery according to a sixth disclosed embodiment of the invention.

FIG. 16 is a side view of a mesh assembly 60 for cosmetic surgery according to a sixth disclosed embodiment of the invention. Referring to FIG. 16, a mesh assembly 60 for cosmetic surgery according to the sixth disclosed embodiment of the invention can include a mesh sleeve 100 and a needle 400, 600, 610, with the core 200, protrusions 250, and cover film 310, 320 omitted. In this case, the needle 600 can be a suture needle having a curved shape, and the mesh sleeve 100 can be used in lieu of a suture thread.

The embodiments of the invention presented above provide a mesh assembly 10, 20, 30, 40 that has a drastically greater strength compared to a regular surgical thread and can be joined to the surgical site with high strength. The mesh assembly 10, 20, 30, 40 can thus provide greater utility in procedures such as tissue lifting.

A mesh assembly according to an embodiment of the invention makes it possible to more precisely adjust the positions where the protrusions extending out of the mesh sleeve join the surrounding tissue at the surgical site and thus can significantly increase the success rate of the procedure.

While the foregoing provides a description with reference to an embodiment of the present invention, it should be appreciated that a person having ordinary skill in the relevant field of art would be able to make various modifications and alterations to the present invention without departing from the spirit and scope of the present invention set forth in the scope of claims below.

What is claimed is:
1. A mesh assembly comprising:
   a mesh sleeve including a plurality of helical string members, the string members entwined in intersecting directions to form a passage having a particular diameter within the mesh sleeve;
   a core extending along a first direction and positioned within the passage;
   a protrusion protruding from an outer perimeter of the core in a direction inclined towards one side, the protrusion extending through a gap between the string members to an outside of the mesh sleeve; and
   a cover film positioned between the mesh sleeve and the core and surrounding the protrusion to restrain the protrusion such that the protrusion lies within the passage,
   wherein the protrusion is configured to protrude out of the mesh sleeve when the cover film is removed after the mesh sleeve is inserted into a surgical site,
   an indentation is formed in the core, an end portion of the protrusion has a curved portion formed in a curved shape on an outer side thereof and has a hook portion formed in a pointy shape on an inner side thereof, and
   the hook portion of the protrusion is inserted in the indentation and the curved portion faces the cover film while the protrusion is restrained by the cover film.

2. The mesh assembly of claim 1, wherein the mesh sleeve is made from a hydrolysable material.

3. The mesh assembly of claim 2, wherein the mesh sleeve is made from a material containing one or more polymer selected from a group consisting of polydioxanone (PDO), polylactic acid (PLA), poly-L-lactide (PLLA), polycaprolactone (PCL), polyhydroxyalkanoate (PHA), polyhydroxybutyrate (PHB), poly-D-lactide, and poly-DL-lactide (PDLLA).

4. The mesh assembly of claim 1, wherein the cover film is wound around the core in a helical form.

5. The mesh assembly of claim 1, wherein the cover film surrounds the core in a form of a tube.

\* \* \* \* \*